US012612586B2

(12) United States Patent
   Inoue et al.

(10) Patent No.: US 12,612,586 B2
(45) Date of Patent: Apr. 28, 2026

(54) CELL CULTURE CONTAINER AND CELL CULTURE SYSTEM

(71) Applicant: Shimadzu Corporation, Kyoto (JP)

(72) Inventors: Tsunehiro Inoue, Kyoto (JP); Toyoyuki Hashimoto, Kyoto (JP); Yasuko Yoneda, Kyoto (JP); Kenji Takubo, Kyoto (JP); Yoichi Fujiyama, Kyoto (JP); Tomoki Ohkubo, Kyoto (JP); Eiichi Ozeki, Kyoto (JP); Ryogo Takai, Kyoto (JP); Hiroomi Goto, Kyoto (JP); Sadamu Tomita, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 535 days.

(21) Appl. No.: 18/022,592

(22) PCT Filed: Jul. 7, 2021

(86) PCT No.: PCT/JP2021/025595
   § 371 (c)(1),
   (2) Date: Feb. 22, 2023

(87) PCT Pub. No.: WO2022/044555
   PCT Pub. Date: Mar. 3, 2022

(65) Prior Publication Data
   US 2023/0313103 A1     Oct. 5, 2023

(30) Foreign Application Priority Data
   Aug. 26, 2020     (JP) ................................. 2020-142616

(51) Int. Cl.
   C12M 1/12         (2006.01)
   C12M 1/00         (2006.01)
   (Continued)

(52) U.S. Cl.
   CPC ............ C12M 25/10 (2013.01); C12M 23/24 (2013.01); C12M 23/38 (2013.01); C12M 29/00 (2013.01); C12M 41/46 (2013.01)

(58) Field of Classification Search
   None
   See application file for complete search history.

(56) References Cited

U.S. PATENT DOCUMENTS

| | | | |
|---|---|---|---|
| 6,794,184 B1 | 9/2004 | Mohr et al. | |
| 2008/0145922 A1* | 6/2008 | Lehmann ............... | C12M 33/04 435/287.9 |

(Continued)

FOREIGN PATENT DOCUMENTS

| | | |
|---|---|---|
| CN | 106103692 | 11/2016 |
| CN | 108699500 | 10/2018 |

(Continued)

OTHER PUBLICATIONS

International Search Report issued Sep. 21, 2021 in International (PCT) Application No. PCT/JP2021/025595.

(Continued)

*Primary Examiner* — Holly Kipouros
(74) *Attorney, Agent, or Firm* — Wenderoth, Lind & Ponack, L.L.P.

(57)                    ABSTRACT

A cell culture container includes: a container body; a cell culture insert having a tubular portion and an oxygen-permeable membrane; and a lid member. The container body is provided with an opening that communicates with an interior of the container body. The tubular portion includes an upper end and a lower end, and is inserted in the opening such that the lower end is located inside the container body. The lower end side of the tubular portion is closed by the membrane. The upper end side of the tubular portion is closed by the lid member. The lid member includes a lower surface that faces toward an interior of the tubular portion.

(Continued)

The lid member is provided with an electrode insertion port and a culture medium outlet port that each communicate with the interior of the tubular portion at the lower surface.

4 Claims, 5 Drawing Sheets

(51) Int. Cl.
    *C12M 1/04*        (2006.01)
    *C12M 1/34*        (2006.01)

(56)                    References Cited

U.S. PATENT DOCUMENTS

| | | | |
|---|---|---|---|
| 2014/0045252 A1 | 2/2014 | Nakajima et al. | |
| 2015/0247112 A1* | 9/2015 | Orr | C12M 29/10 435/395 |
| 2016/0340632 A1 | 11/2016 | Breinlinger et al. | |
| 2017/0067006 A1 | 3/2017 | Obi et al. | |
| 2019/0031994 A1 | 1/2019 | Tanaka et al. | |
| 2019/0382703 A1 | 12/2019 | Katayama et al. | |
| 2022/0340859 A1* | 10/2022 | Ohsaka | G01N 15/1484 |

FOREIGN PATENT DOCUMENTS

| | | | |
|---|---|---|---|
| CN | 110072988 | 7/2019 | |
| EP | 3 546 561 | 10/2019 | |
| KR | 10-1910118 | 10/2018 | |
| TW | M240450 | 8/2004 | |
| WO | 2018/079793 | 5/2018 | |
| WO | 2019/222333 | 11/2019 | |
| WO | WO-2019222333 A1 * | 11/2019 | C12N 5/0679 |

OTHER PUBLICATIONS

Written Opinion of the International Searching Authority issued Sep. 21, 2021 in International (PCT) Application No. PCT/JP2021/025595 with partial English translation.

Extended European Search Report issued Jul. 18, 2025 in European Patent Application No. 21860985.7 (8 pages).

Office Action issued Oct. 30, 2025 in Chinese Patent Application No. 202180052328.6, with English-language Translation (19 pages).

Office Action issued Feb. 15, 2026 in corresponding Chinese Patent Application No. 202180052328.6 (with machine English translation), 18 pages.

* cited by examiner

CELL CULTURE CONTAINER AND CELL CULTURE SYSTEM

TECHNICAL FIELD

The present invention relates to a cell culture container and a cell culture system.

BACKGROUND ART

A cell culture container described in PTL 1 (WO 2018/079793) includes a culture tank and a cell culture insert. The culture tank is provided with an opening that communicates with the interior of the culture tank. The cell culture insert has a tubular portion and a porous membrane (hereinafter called "membrane") that closes a lower end of the tubular portion. The tubular portion is inserted in the opening such that the membrane is located inside the culture tank. A first culture medium is stored in the tubular portion, and a second culture medium is stored in the culture tank. Cells are cultured on the membrane.

CITATION LIST

Patent Literature

PTL 1: WO 2018/079793

SUMMARY OF INVENTION

Technical Problem

The cell culture container described in PTL 1 is not intended for replacement of the first culture medium and monitoring of the condition of the cells being cultured on the membrane during an experiment.

The present invention provides a cell culture container by which the condition of cells on a membrane can be accurately monitored while a culture medium is replaced.

Solution to Problem

A cell culture container of the present invention includes: a container body; a cell culture insert having a tubular portion and an oxygen-permeable membrane; and a lid member. The container body is provided with an opening that communicates with an interior of the container body. The tubular portion includes an upper end and a lower end, and is inserted in the opening such that the lower end is located inside the container body. The lower end side of the tubular portion is closed by the membrane.

The upper end side of the tubular portion is closed by the lid member. The lid member includes a lower surface that faces toward an interior of the tubular portion. The lid member is provided with an electrode insertion port and a culture medium outlet port that each communicate with the interior of the tubular portion at the lower surface. A distance between the membrane and the lower surface monotonically increases from a lower surface side end of the electrode insertion port toward a lower surface side end of the culture medium outlet port.

Advantageous Effects Of Invention

According to the cell culture container of the present invention, the condition of cells on the membrane can be accurately monitored while a culture medium is replaced.

DESCRIPTION OF EMBODIMENTS

Figure 1:
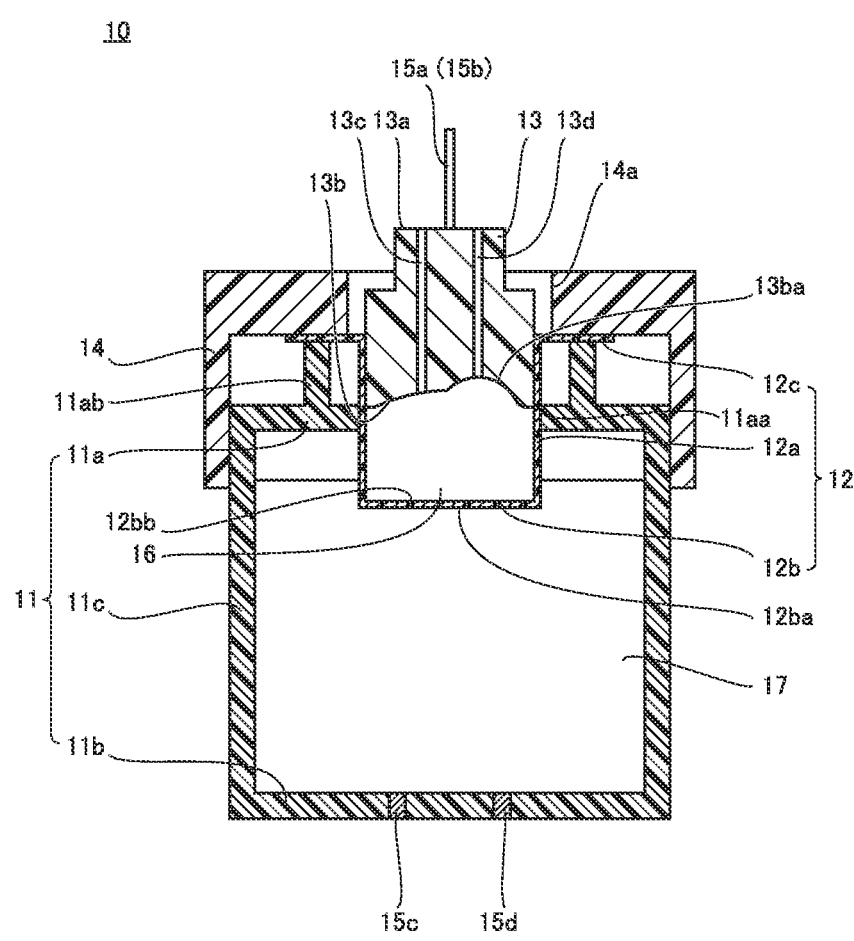
FIG. 1 is a cross-sectional view of a cell culture container 10.

An embodiment will be described in detail with reference to the drawings. In the following, the same or corresponding parts are designated by the same reference characters, and the same description will not be repeated.

(Configuration of Cell Culture Container According to Embodiment)

A configuration of a cell culture container (hereinafter called "cell culture container 10") according to the embodiment is described below.

FIG. 1 is a cross-sectional view of cell culture container 10. As shown in FIG. 1, cell culture container 10 includes a container body 11, a cell culture insert 12, a lid member 13, a lid member 14, an electrode 15a and an electrode 15b, and an electrode 15c and an electrode 15d.

Container body 11 has an upper wall 11a, a bottom wall 11b, and a side wall 11c. Upper wall 11a and bottom wall 11b are spaced from and face each other. Side wall 11c is contiguous at its upper end to upper wall 11a and at its lower end to bottom wall 11b. Upper wall 11a, bottom wall 11b and side wall 11c define an internal space of container body 11. Container body 11 is made of a resin material, for example.

Upper wall 11a is provided with an opening 11aa. Opening 11aa passes through upper wall 11a in a thickness direction. Put another way, opening 11aa communicates with the interior of container body 11. Upper wall 11a has an erect portion 11ab. Erect portion 11ab extends to the side opposite to bottom wall 11b (upward). Erect portion 11ab is located around opening 11aa.

Cell culture insert 12 has a tubular portion 12a, a membrane 12b, and a flange portion 12c.

Tubular portion 12a has a tubular shape. In a cross-sectional view orthogonal to a direction from an upper end of tubular portion 12a toward a lower end of tubular portion 12a, tubular portion 12a has an annular shape, for example. The upper end of tubular portion 12a is open. The lower end of tubular portion 12a is closed by membrane 12b.

Tubular portion 12a is inserted in opening 11aa such that its lower end is located inside container body 11 (such that membrane 12b is located inside container body 11). The space between tubular portion 12a and opening 11aa is hermetically sealed by an appropriate method.

Membrane 12b is oxygen-permeable. Membrane 12b is, for example, a track etched membrane made of polycarbonate. Membrane 12b has a first main surface 12ba and a second main surface 12bb. Second main surface 12bb is opposite to first main surface 12ba.

First main surface 12ba is a surface that faces toward the interior of container body 11. Second main surface 12bb is a surface that faces toward the interior of tubular portion 12a. Put another way, the internal space of container body 11 is partially defined by first main surface 12ba, and the internal space of tubular portion 12a is partially defined by second main surface 12bb.

Cells are cultured on second main surface 12*bb*. The cells are, for example, intestinal epithelial cells that form tight junctions on second main surface 12*bb*. Caco-2 cells are a specific example of the cells.

A first culture medium 16 is stored in tubular portion 12*a*. First culture medium 16 contains bacteria. The bacteria are anaerobic bacteria, for example. A second culture medium 17 is stored in container body 11. First culture medium 16 has a lower dissolved oxygen concentration than that of second culture medium 17. Put another way, first culture medium 16 is an anaerobic culture medium, and second culture medium 17 is an aerobic culture medium.

As described above, membrane 12*b* is oxygen-permeable. Therefore, oxygen in second culture medium 17 permeates through membrane 12*b* and is supplied to the cells being cultured on second main surface 12*bb*. The cells can thus be cultured on second main surface 12*bb*.

Flange portion 12*c* is at the upper end side of tubular portion 12*a*. Flange portion 12*c* extends from an outer circumferential surface of tubular portion 12*a* in a direction crossing the direction from the upper end of tubular portion 12*a* toward the lower end of tubular portion 12*a*. Cell culture insert 12 is restricted from moving in a direction from upper wall 11*a* toward bottom wall 11*b* by flange portion 12*c* being supported by erect portion 11*ab*.

Lid member 13 is made of a resin material, for example. This resin material is a silicone resin, for example. Lid member 13 is inserted into tubular portion 12*a* from the upper end side of tubular portion 12*a*. As a result, the upper end side of tubular portion 12*a* is closed by lid member 13.

Lid member 13 has an upper surface 13*a* and a lower surface 13*b*. Lower surface 13*b* is opposite to upper surface 13*a*. Lower surface 13*b* faces toward the interior of tubular portion 12*a*.

Figure 2:
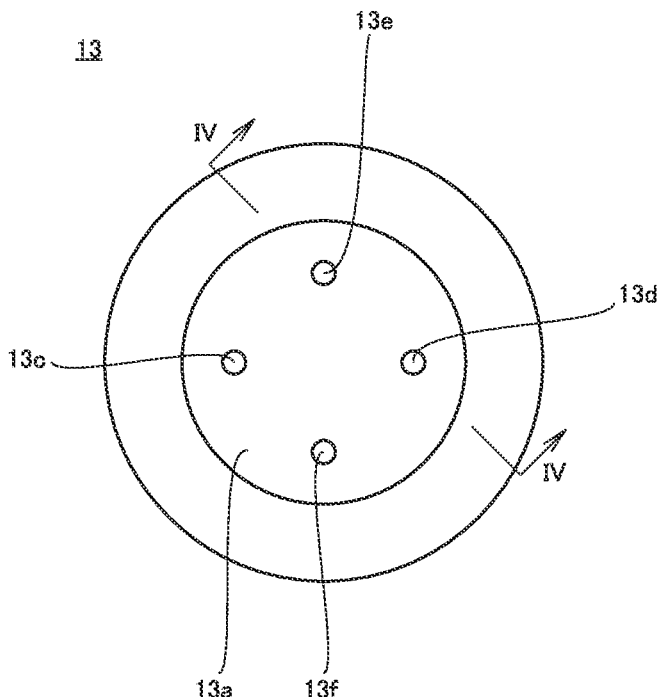
FIG. 2 is a plan view of a lid member 13.
Figure 3:
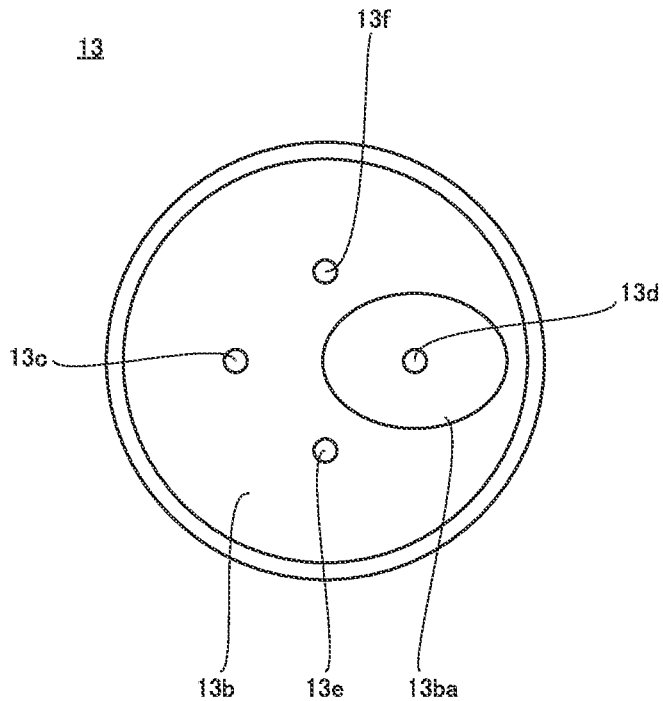
FIG. 3 is a bottom view of lid member 13.
Figure 4:
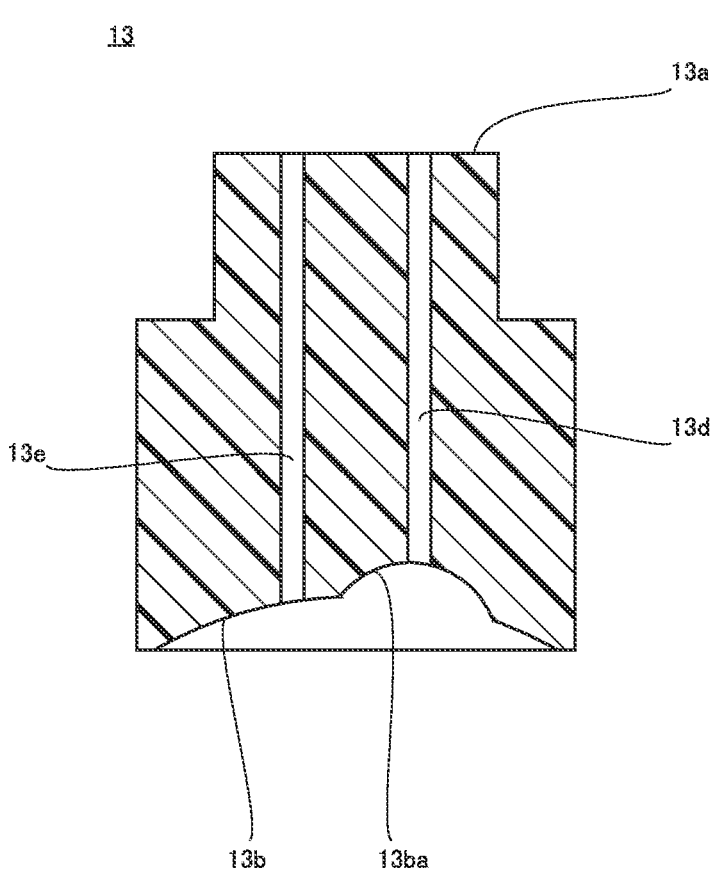
FIG. 4 is a cross-sectional view taken along a line IV-IV in FIG. 2.

FIG. 2 is a plan view of lid member 13. FIG. 3 is a bottom view of lid member 13. FIG. 4 is a cross-sectional view taken along a line IV-IV in FIG. 2. As shown in FIGS. 1 to 4, lower surface 13*b* is preferably a curved surface protruding toward upper surface 13*a*. Lower surface 13*b* is preferably provided with a recess 13*ba*. Lower surface 13*b* is more recessed toward upper surface 13*a* at recess 13*ba* than at a portion around recess 13*ba*. Recess 13*ba* is, for example, a curved surface protruding toward upper surface 13*a*.

Lid member 13 is provided with a culture medium inlet port 13*c*, a culture medium outlet port 13*d*, an electrode insertion port 13*e*, and an electrode insertion port 13*f*. Culture medium inlet port 13*c*, culture medium outlet port 13*d*, electrode insertion port 13*e* and electrode insertion port 13*f* pass through lid member 13 from upper surface 13*a* toward lower surface 13*b*, for example. Put another way, culture medium inlet port 13*c*, culture medium outlet port 13*d*, electrode insertion port 13*e* and electrode insertion port 13*f* communicate with the interior of tubular portion 12*a* at their ends on the lower surface 13*b* side.

First culture medium 16 is introduced into tubular portion 12*a* through culture medium inlet port 13*c*. First culture medium 16 stored in tubular portion 12*a* is discharged through culture medium outlet port 13*d*.

The distance between lower surface 13*b* and membrane 12*b* monotonically increases from the end of electrode insertion port 13*e* on the lower surface 13*b* side toward the end of culture medium outlet port 13*d* on the lower surface 13*b* side. Put another way, the distance between lower surface 13*b* and upper surface 13*a* monotonically decreases from the end of electrode insertion port 13*e* on the lower surface 13*b* side toward the end of culture medium outlet port 13*d* on the lower surface 13*b* side.

Although not shown, the distance between lower surface 13*b* and membrane 12*b* monotonically increases (the distance between lower surface 13*b* and upper surface 13*a* monotonically decreases) from the end of electrode insertion port 13*f* on the lower surface 13*b* side toward the end of culture medium outlet port 13*d* on the lower surface 13*b* side.

The distance between lower surface 13*b* and membrane 12*b* monotonically decreases (the distance between lower surface 13*b* and upper surface 13*a* monotonically decreases) from the end of culture medium inlet port 13*c* on the lower surface 13*b* side toward the end of culture medium outlet port 13*d* on the lower surface 13*b* side.

The end of culture medium outlet port 13*d* on the lower surface 13*b* side is disposed in recess 13*ba*. The end of culture medium outlet port 13*d* on the lower surface 13*b* side is preferably disposed at the apex of the curved surface forming recess 13*ba*. The apex of the curved surface forming recess 13*ba* is the position of recess 13*ba* where the distance from upper surface 13*a* is the smallest.

Lid member 14 is removably attached to container body 11. More specifically, lid member 14 is attached to container body 11 so as to sandwich flange portion 12*c* between lid member 14 and erect portion 11*ab*. This prevents cell culture insert 12 from falling out of container body 11. Lid member 14 is provided with an opening 14*a*. Upper surface 13*a* is exposed at opening 14*a*.

Electrode 15*a* is inserted in electrode insertion port 13*e*. As a result, electrode 15*a* has one end electrically connected to first culture medium 16 stored in tubular portion 12*a*. Electrode 15*a* has the other end located outside of lid member 13.

Electrode 15*b* is inserted in electrode insertion port 13*f*. As a result, electrode 15*b* has one end electrically connected to first culture medium 16 stored in tubular portion 12*a*. Electrode 15*b* has the other end located outside of lid member 13.

Electrode 15*c* and electrode 15*d* are embedded in container body 11. More specifically, electrode 15*c* and electrode 15*d* are embedded in bottom wall 11*b*.

Electrode 15*c* and electrode 15*d* are electrically connected to second culture medium 17 stored in container body 11. Electrode 15*c* and electrode 15*d* are exposed outside of container body 11.

(Configuration of Cell Culture System According to Embodiment)

A configuration of a cell culture system (hereinafter called "cell culture system 100") according to the embodiment is described below.

Figure 5:
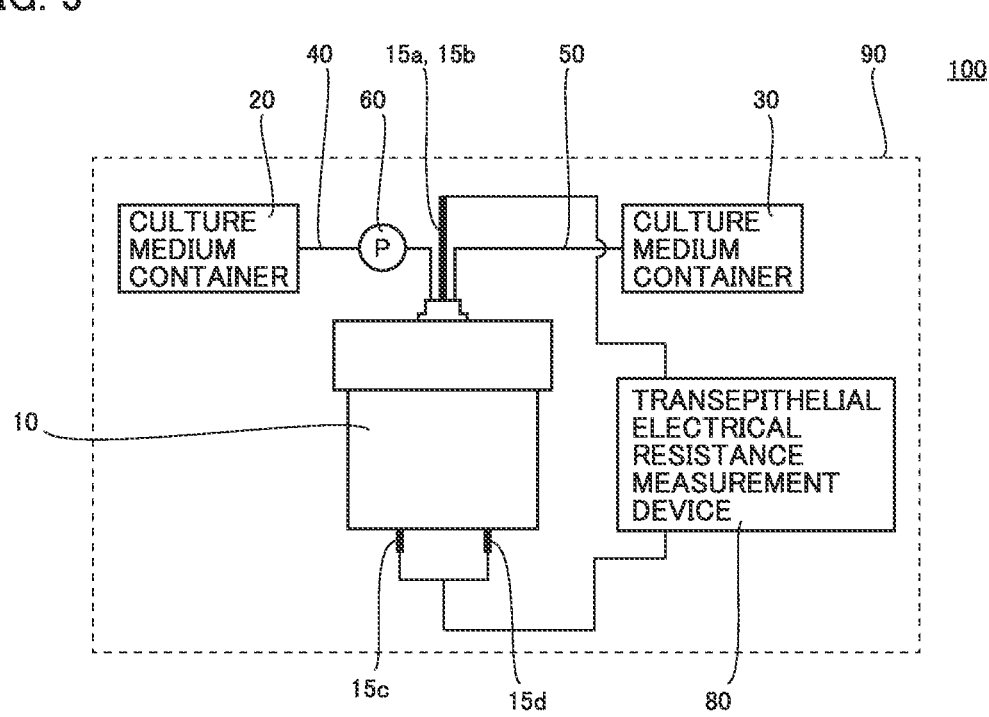
FIG. 5 is a schematic diagram of a cell culture system 100.

FIG. 5 is a schematic diagram of cell culture system 100. As shown in FIG. 5, cell culture system 100 includes cell culture container 10, a culture medium container 20, a culture medium container 30, a tube 40, a tube 50, a pump 60, and a transepithelial electrical resistance measurement device 80. Cell culture container 10, culture medium container 20, culture medium container 30, tube 40, tube 50, pump 60 and transepithelial electrical resistance measurement device 80 are housed in an anaerobic chamber 90.

First culture medium 16 is stored in culture medium container 20. Tube 40 is connected at one end to culture medium container 20 and at the other end to culture medium inlet port 13*c*. As a result, the interior of tubular portion 12*a* and culture medium container 20 are connected via tube 40. Pump 60 is attached to tube 40. Pump 60 is a tube pump, for example. By driving pump 60, first culture medium 16 stored in culture medium container 20 is introduced into tubular portion 12a through culture medium inlet port 13c via tube 40.

Tube 50 is connected at one end to culture medium container 30 and at the other end to culture medium outlet port 13d. As a result, the interior of tubular portion 12a and culture medium container 30 are connected via tube 50. By driving pump 60, first culture medium 16 stored in tubular portion 12a is discharged into culture medium container 30 through culture medium outlet port 13d via tube 50. In other words, the supply of first culture medium 16 to culture medium container 30 and the collection of first culture medium 16 from culture medium container 30 are performed by pump 60.

Transepithelial electrical resistance measurement device 80 has a first terminal and a second terminal. The first terminal of transepithelial electrical resistance measurement device 80 is connected to electrode 15a and electrode 15b. The second terminal of transepithelial electrical resistance measurement device 80 is connected to electrode 15c and electrode 15d. Transepithelial electrical resistance measurement device 80 measures an electrical resistance value between electrode 15a, electrode 15b and electrode 15c, electrode 15d by a four-terminal method, for example.

The electrical resistance value between electrode 15a, electrode 15b and electrode 15c, electrode 15d varies depending on whether or not the cells being cultured on second main surface 12bb are forming tight junctions. By measuring the above electrical resistance value using transepithelial electrical resistance measurement device 80, therefore, it can be determined whether or not the cells being cultured on second main surface 12bb are forming tight junctions.

(Effects of Cell Culture Container According to Embodiment)

Effects of cell culture container 10 are described below.

In cell culture container 10, first culture medium 16 can be introduced into tubular portion 12a through culture medium inlet port 13c, and first culture medium 16 can be discharged out of tubular portion 12a through culture medium outlet port 13d. Thus, according to cell culture container 10, first culture medium 16 can be replaced during an experiment to thereby suppress excessive growth of bacteria inside tubular portion 12a, thus allowing the experiment to continue for a long period of time.

As a result of the replacement of first culture medium 16, air bubbles may be introduced into tubular portion 12a together with first culture medium 16. In addition, the bacteria contained in first culture medium 16 may produce air bubbles inside tubular portion 12a. These air bubbles adhere to electrode 15a and electrode 15b, causing fluctuations in the electrical resistance value measured by transepithelial electrical resistance measurement device 80. In other words, the adhesion of these air bubbles to electrode 15a and electrode 15b makes it difficult to accurately monitor the condition of the cells being cultured on membrane 12b.

In cell culture container 10, however, the distance between lower surface 13b and membrane 12b monotonically increases from the end of electrode insertion port 13e (electrode insertion port 13f) on the lower surface 13b side toward the end of culture medium outlet port 13d on the lower surface 13b side.

As a result, even if the above air bubbles adhere to electrode 15a (electrode 15b), they tend to move along lower surface 13b toward culture medium outlet port 13d due to buoyancy, to be discharged through culture medium outlet port 13d. Thus, according to cell culture container 10, the condition of the cells on membrane 12b can be accurately monitored while first culture medium 16 is replaced.

In cell culture container 10, if lower surface 13b is provided with recess 13ba, the above air bubbles tend to collect in the recess. In this case, therefore, the above air bubbles are more readily discharged through culture medium outlet port 13d.

In addition, in cell culture container 10, if the distance between lower surface 13b and membrane 12b monotonically increases from the end of culture medium inlet port 13c on the lower surface 13b side toward the end of culture medium outlet port 13d on the lower surface 13b side, the air bubbles introduced through culture medium inlet port 13c together with first culture medium 16 are readily discharged through culture medium outlet port 13d along lower surface 13b due to buoyancy.

While the embodiment of the present invention has been described above, the embodiment described above can be modified in various manners. In addition, the scope of the present invention is not limited to the embodiment described above. It is intended that the scope of the present invention is defined by claims and encompasses all modifications equivalent in meaning and scope to the claims.

REFERENCE SIGNS LIST

100 cell culture system; 10 cell culture container; 11 container body; 11a upper wall; 11aa opening; flab erect portion; 11b bottom wall; 11c side wall; 12 cell culture insert; 12a tubular portion; 12b membrane; 12ba first main surface; 12bb second main surface; 12c flange portion; 13 lid member; 13a upper surface; 13b lower surface; 13ba recess; 13c culture medium inlet port; 13d culture medium outlet port; 13e, 13f electrode insertion port; 14 lid member; 14a opening; 15a, 15b, 15c, 15d electrode; 16 first culture medium; 17 second culture medium; 20, 30 culture medium container; 40, 50 tube; 60 pump; 80 transepithelial electrical resistance measurement device.

The invention claimed is:

1. A cell culture container comprising:
a container body;
a second electrode;
a cell culture insert having a tubular portion and an oxygen-permeable membrane; and
a lid member, wherein
the container body is provided with an opening that communicates with an interior of the container body,
the second electrode is embedded in the container body so as to be electrically connected to a second culture medium stored in the interior of the container body,
the tubular portion includes an upper end and a lower end, and is inserted in the opening such that the lower end is located inside the container body,
the lower end of the tubular portion is closed by the membrane,
the upper end of the tubular portion is closed by the lid member,
the lid member includes a lower surface that faces toward an interior of the tubular portion,
the lid member is provided with a culture medium inlet port through which a first culture medium is supplied into the tubular portion, an electrode insertion port into which a first electrode is inserted so as to electrically connect the first culture medium, and a culture medium outlet port, each of the electrode insertion port, the culture medium inlet port and the culture medium outlet port communicates with the interior of the tubular portion at the lower surface, and a distance between the membrane and the lower surface monotonically increases from a lower surface side end of the electrode insertion port toward a lower surface side end of the culture medium outlet port.

2. The cell culture container according to claim 1, wherein the lid member includes an upper surface opposite to the lower surface, the lower surface is a curved surface protruding toward the upper surface, the lower surface is provided with a recess, the lower surface is more recessed toward the upper surface at the recess than at a portion of the lower surface around the recess, and the lower surface side end of the culture medium outlet port is located in the recess.

3. The cell culture container according to claim 1, wherein the culture medium inlet port communicates with the interior of the tubular portion at the lower surface, and the distance between the membrane and the lower surface monotonically increases from a lower surface side end of the culture medium inlet port toward the lower surface side end of the culture medium outlet port.

4. A cell culture system comprising:

the cell culture container according to claim 3;

a first tube connected to the culture medium inlet port;

a second tube connected to the culture medium outlet port;

a pump that introduces the first culture medium into the tubular portion via the first tube, and discharges the first culture medium from the interior of the tubular portion via the second tube; and a transepithelial electrical resistance measurement device that measures an electrical resistance value between the first electrode and the second electrode.

\*    \*    \*    \*    \*